United States Patent
DuVall et al.

(10) Patent No.: US 9,459,230 B2
(45) Date of Patent: Oct. 4, 2016

(54) MATRIX STABILITY COMPOSITIONS, TEST ELEMENTS, TEST SYSTEMS AND METHODS OF USE THEREOF

(71) Applicant: Roche Diabetes Care, Inc., Indianapolis, IN (US)

(72) Inventors: Stacy H. DuVall, Indianapolis, IN (US); Sibylle Kachel, Karlsruhe (DE); Georgeta C. Lica, Indianapolis, IN (US); Wilhelm Schabel, Karlsruhe (DE); Philip Scharfer, Eggenstein-Leopoldshafen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 14/639,621

(22) Filed: Mar. 5, 2015

(65) Prior Publication Data

US 2015/0177178 A1 Jun. 25, 2015

Related U.S. Application Data

(63) Continuation of application No. PCT/EP2013/068238, filed on Sep. 4, 2013.

(60) Provisional application No. 61/697,535, filed on Sep. 6, 2012.

(51) Int. Cl.
*G01N 27/327* (2006.01)
*C12Q 1/00* (2006.01)

(52) U.S. Cl.
CPC ........... *G01N 27/3274* (2013.01); *C12Q 1/004* (2013.01); *G01N 27/3272* (2013.01); *Y10T 29/49002* (2015.01)

(58) Field of Classification Search
CPC ..................... G01N 27/3274; G01N 27/3272; C12Q 1/004; Y10T 29/49002
See application file for complete search history.

(56) References Cited

U.S. PATENT DOCUMENTS

| 5,128,015 A | 7/1992 | Szuminsky et al. |
| 5,264,103 A * | 11/1993 | Yoshioka ............... C12Q 1/004 204/403.1 |
| 5,286,362 A | 2/1994 | Hoenes et al. |
| 8,008,037 B2 * | 8/2011 | Wilsey ................... C12Q 1/004 435/26 |
| 2008/0031778 A1 | 2/2008 | Kramer |

FOREIGN PATENT DOCUMENTS

| EP | 1174716 B1 | 10/2004 |
| GB | 2499838 A | 9/2013 |
| WO | 97/27483 A1 | 7/1997 |
| WO | 01/08784 A1 | 2/2001 |
| WO | 02/50609 A2 | 6/2002 |
| WO | 02/083273 A1 | 10/2002 |
| WO | 2006/052748 A2 | 5/2006 |
| WO | 2008/130680 A1 | 10/2008 |

OTHER PUBLICATIONS

S. Tsujimura, et al. "Novel FAD-Dependent Glucose Dehydrogenase for a Dioxygen-Insensitive Glucose Biosensor" Bioscience, Biotechnology, and Biochemistry vol. 70, No. 3, Jan. 2006, p. 654-659.*
Kachel, et al., "Sorption isotherms of mixtures of polymers, proteins and electrolytes—measurement data and model predications", Thin Film Technology, Institute of Thermal Process Engineering, Karlsruhe Institute of Technology, pp. 1-18, Jun. 2013, Chemical Engineering and Processing:Process Intensification.

* cited by examiner

*Primary Examiner* — J. Christopher Ball

(57) ABSTRACT

Reagent matrices and methods are disclosed for improving the stability of test elements with respect to degradation by humidity in the air. The reagent matrices and methods are based upon using an effective amount of a deliquescent material to decrease the sorption of water from the air by other components of a reagent matrix. When the test element is a glucose-specific test strip, and the reagent matrix can include a glucose dehydrogenase enzyme and/or a flavin adenine dinucleotide cofactor, a nitrosoaniline mediator, and a film former, where the deliquescent material may include a salt such as sodium chloride in an amount effective to absorb water from the atmosphere at a rate that is faster than the rate at which the other components of the reagent matrix absorb water from the atmosphere.

15 Claims, 7 Drawing Sheets

MATRIX STABILITY COMPOSITIONS, TEST ELEMENTS, TEST SYSTEMS AND METHODS OF USE THEREOF

CROSS-REFERENCE TO RELATED APPLICATIONS

This patent application is a continuation of Int'l Patent Application No. PCT/EP2013/068238 (filed 4 Sep. 2013), which claims priority to and the benefit of U.S. Provisional Patent Application No. 61/697,535 (6 Sep. 2012). Each patent application is incorporated herein by reference as if set forth in its entirety.

TECHNICAL FIELD

This patent application relates generally to chemistry and medicine/medical diagnostics, and more particularly, it relates to matrix stability compositions, test elements, test systems, and methods of protecting a dry-film reagent matrix of test elements from degradation by atmospheric humidity or water vapor.

BACKGROUND

As the number of individuals having diabetes and similar medical conditions increases, self-monitoring of blood glucose levels has become a common practice. The purpose of monitoring the blood glucose level is to determine its concentration and then to take corrective action based upon whether the concentration is too high or too low, thereby bringing the blood glucose level back within a normal range. The failure to take corrective action can have serious medical implications, so daily self-monitoring of blood glucose is a fact of everyday life for diabetic individuals. Failure to test blood glucose levels properly and on a regular basis can result in serious diabetes-related complications, including cardiovascular disease, kidney disease, nerve damage and blindness.

Biosensors, such as test elements, are available to permit diabetic individuals to test glucose levels in a small blood sample. Common meter designs use disposable test elements that, in combination with the meter, electrochemically or optically measure the presence or concentration of glucose in the blood sample. The information typically is displayed as a blood glucose value and perhaps the time and date that the measurement was performed. This information is, in most cases, sufficient to allow diabetic individuals to adjust their dietary intake and/or insulin dosage, and in the case of low glucose values, may indicate a need for intake of sugar to avoid hypoglycemia.

Electrochemically measuring an analyte may be achieved by dosing a test element with a sample containing the analyte (e.g., glucose in an aqueous blood sample) to initiate a chain of reactions such as the chain shown below for glucose.

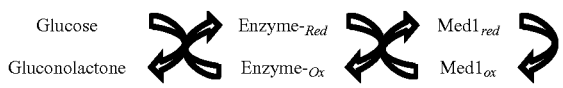

By applying a potential difference between working and counter electrodes of the test element, the reduced form of a mediator is converted to its oxidized form. A current associated with this reaction is proportional with a mass of reduced mediator, and consequently with the glucose concentration.

Exposing test elements, such as glucose test strips, to high humidity conditions, however, may cause the mediator to degrade to the reduced form or to other products that are electrochemically active in the same potential range. Additionally, high humidity may cause the enzyme to degrade to a reduced form, and the reduced enzyme may react with the mediator, producing mediator in its reduced form.

In this regard, electroactive degradation products can accumulate at the electrode surface, and a corresponding conversion under an applied potential will result in current generation even in the absence of a substrate (i.e., a blank current). This current can add to the current generated by the glucose reaction resulting in a positively biased result or increased strip failure rate.

The components of a test element's reagent matrix often are selected to dissolve quickly in an aqueous sample, thus providing a fast reaction time and a quick display of the result for the user. However, this provides the undesired consequence of making the reagent matrix susceptible to degradation by environmental humidity, thus compromising the shelf stability of disposable test elements.

Accordingly, methods of decreasing a test element's sensitivity to environmental conditions are desired. While test elements can be packaged and distributed in containers configured to prevent undesired ingress of moisture from the atmosphere or other sources, and while such test elements can be packaged in containers with desiccant materials incorporated within the container (such as in the lid or cap of the container) or in an insert that is left in the container with the test elements, known methods have not been effective for eliminating the risks of degradation.

For the foregoing reasons, there is a need for compositions and methods of improving the stability of test elements and test systems, and more particularly of glucose test strips, under unfavorable ambient measurement or environmental conditions, especially high humidity.

BRIEF SUMMARY

An inventive concept described herein includes providing at least one deliquescent material in a dry-film reagent matrix used in connection with analytical test elements. This inventive concept is achieved by selecting at least one deliquescent material having an ability to absorb water from the atmosphere/air in which the test elements may be exposed or stored at a rate that is faster than the rate at which the other components of the dry-film reagent matrix absorb water from the atmosphere/air. The inventive concept can be incorporated into exemplary dry-film reagent matrices, test elements, test systems and methods as described herein and in more detail below.

For example, dry-film reagent matrices are provided that can include at least one mediator, at least one enzyme system, and at least one deliquescent material in an amount effective to absorb water from the atmosphere/environment (i.e., air) when compared to water absorption properties and rates of the other components of the dry-film reagent matrix, thus protecting the other components from degradation by humidity/water when a relative humidity exceeds a deliquescence point of the at least one deliquescent material.

The enzyme system may include a glucose dehydrogenase (GDH) enzyme and/or a flavin adenine dinucleotide (FAD) cofactor. Likewise, the mediator may include a nitrosoaniline mediator. In some instances, the dry-film reagent matrices also include a film former such as polyvinylpyrrolidone (PVP).

The deliquescent material can absorb water when the relative humidity exceeds any predetermined level, such as about 40%, about 50%, about 60%, about 70%, about 75%, or even about 80% or more. Alternatively, the deliquescent material can have a deliquescence point between about 50% relative humidity and about 80% relative humidity. In particular, the deliquescent material has a deliquescence point of about 75% relative humidity. Regardless, the deliquescent material should be provided in an amount effective to absorb water from the atmosphere at a rate that is faster than the rate at which the other components of the dry-film reagent matrix absorb water from the atmosphere, especially when the relative humidity in the atmosphere exceeds about 75%.

The deliquescent material may be one or more of sodium chloride, calcium chloride, magnesium chloride, zinc chloride, potassium carbonate, potassium phosphate, carnallite, ferric ammonium citrate, potassium hydroxide, and sodium hydroxide.

In addition, test elements are provided for determining a presence or concentration of an analyte of interest, where the test elements include a dry-film reagent matrix as described herein. The test elements also can include a base/supporting substrate and at least one working electrode (WE) and at least one counter electrode (CE) disposed thereupon, although additional electrodes may be included, such as sample sufficiency electrodes and the like. The dry-film reagent matrix extends between the WE and the CE, and thus is configured for an electrode reaction. In some instances, the test element may be configured as a glucose test strip and thus have a glucose-specific dry-film reagent matrix thereon that includes an enzyme system and a mediator as described herein.

In view of the foregoing, methods are provided for improving stability of a test element with respect to degradation of reagent components by humidity in the air, where the test element includes a base/supporting substrate, at least one WE, at least one CE, and a dry-film reagent matrix as described herein that extends between the WE and CE, which is configured for an electrode reaction. The dry-film reagent matrix thus includes a deliquescent material selected and in an amount effective to decrease the sorption of water from the air by other components of the dry-film reagent matrix.

Also provided are methods for improving the stability of a dry-film reagent matrix of an electrochemical test element that includes providing in a dry-film reagent matrix as described herein. The dry-film reagent matrix thus includes a deliquescent material selected and in an amount effective to decrease the sorption of water from the air by other components of the dry-film reagent matrix.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Figure 1:
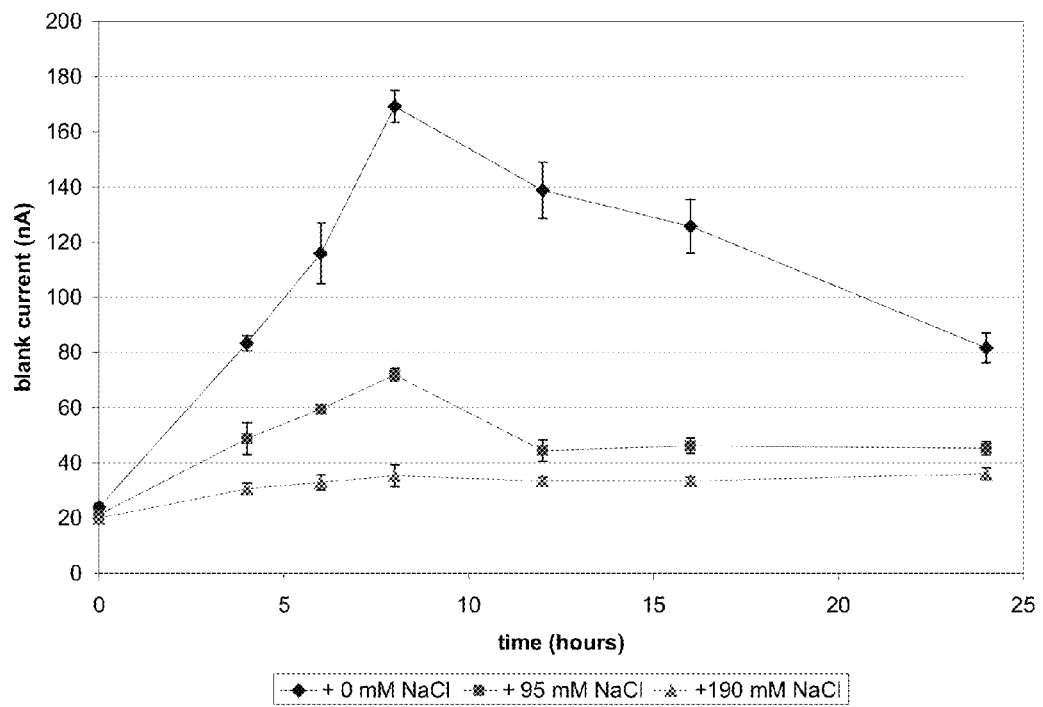
FIG. 1 shows a graph of the blank current (nA) over time for strips having varying amounts of sodium chloride (NaCl) added to the reagent mixture. The strips were dosed with buffer solution and exposed to high heat and humidity conditions (30° C./80% RH).

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The compositions, test elements, test systems and methods now will be described more fully hereinafter with reference to the accompanying drawings, in which some, but not all embodiments of the inventive concept are shown. Indeed, the compositions, test elements, test systems and methods may be embodied in many different forms and should not be construed as limited to the embodiments set forth herein; rather, these embodiments are provided so that this disclosure will satisfy applicable legal requirements.

Likewise, many modifications and other embodiments of the compositions, test elements, systems and methods described herein will come to mind to one of skill in the art to which the disclosure pertains having the benefit of the teachings presented in the foregoing descriptions and the associated drawings. Therefore, it is to be understood that the compositions, test elements, test systems and methods are not to be limited to the specific embodiments disclosed and that modifications and other embodiments are intended to be included within the scope of the appended claims.

Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the compositions, test elements, test systems and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Overview

Glucose-specific test elements generally include a dry-film reagent matrix that includes at least an enzyme/cofactor system and a mediator to electrochemically or optically determine glucose presence or concentration in a body fluid sample such as blood. When such test elements are exposed to high humidity for extended periods of time, however, they tend to lose their functionality or become unstable. The present disclosure addresses that problem by formulating the dry-film reagent matrix to include a deliquescent material that absorbs water from the atmosphere at a selected humidity level, thereby preventing water from degrading other dry-film reagent matrix components. For example, the deliquescent material can be selected to protect the reagent components when exposed to a defined relative humidity, such as when the relative humidity in the atmosphere exceeds about 75%. The deliquescent material can be a salt, especially sodium chloride. Other known deliquescent materials include, but are not limited to, calcium chloride, magnesium chloride, zinc chloride, potassium carbonate, potassium phosphate, carnallite, ferric ammonium citrate, potassium hydroxide, and sodium hydroxide.

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The dry-film reagent matrices and methods described herein have particular utility when used with test elements (e.g., a glucose test strip) having dry-film reagent systems that may degrade if exposed to excessive humidity, such as a relative humidity of about 75%, or even about 70% or less. For example, commonly-used glucose reaction mediators may degrade when exposed to humidity (water) in the air, producing a reduced form or other products that are electrochemically active and can result in a blank current measured by the test meter. Similarly, an enzyme may degrade to a reduced form, then reducing the mediator and presenting that problem by this route. The issue is exacerbated because the reagent matrix needs a degree of hydrophilicity to provide quick wetting of the reagent (and thus, a quick test readout). This issue is specifically present when PVP-containing materials are used as a film former for a glucose-specific reagent system. PVP adsorbs moisture from the air—bringing it into contact with the reagent system.

The problem noted above is thus addressed herein by adding a component to the dry-film reagent matrix that causes it as a whole to adsorb less water. While the inventive concept is illustrated herein by adding a deliquescent material such as sodium chloride to a glucose reagent system including FAD-GDH (coenzyme-dependent enzyme) and nitrosoaniline (mediator), it is contemplated to extend to and function equivalently with other reagent systems and other deliquescent materials.

In view thereof, the inventive concept principally can be incorporated into biosensors, especially test elements such as a glucose-specific test strips. Such test elements typically have at least one WE and at least one CE disposed upon a substrate, and are provided with a dry-film reagent matrix to electrochemically analyze for a presence or concentration of the analyte of interest. However, other devices and processes of this kind are within the scope of the present disclosure, which may utilize one or more alternative test elements. These test elements are known and available in different forms, to which the present disclosure as a whole is applicable. For example, test elements in the form of test strips, test tapes, test disks, foldable test elements (e.g., according to the Leporello principle) and other forms as are known to one of skill in the art. Hereinafter, while the inventive concept will be described substantially with reference to test elements such as test strips, it is to be appreciated that other embodiments also are possible and are intended to be within the scope of the disclosure.

Test elements typically include at least one test field having a test field surface. As used herein, "test field" means a two- or three-dimensional region of the test element, which region is usable in principle for detecting the analyte of interest, which can be carried out qualitatively and/or quantitatively. The test field may be a dry test field, and may include at least one detection reagent selected to carry out a detectable reaction in the presence of the analyte of interest.

In some instances, a dry-film reagent matrix of the test field of the test element includes at least an enzyme system. In some instances, the enzyme system may be glucose dehydrogenase enzyme (GDH) and/or flavin adenine dinucleotide cofactor (FAD), and the mediator may be a nitrosoaniline mediator. The reagent matrix also can include a film former, which may be polyvinylpyrrolidone (PVP). Examples of other glucose-specific enzymatic detection reagents include, but are not limited to, deoxy reductases (e.g., GlucDOR/PQQ), dehydrogenases, oxidases, or similar enzymes such as, for example, glucose oxidase (GOD).

The mediator may be any chemical species (generally electroactive), which can participate in a reaction scheme involving an enzyme, an analyte, and optionally a cofactor (and reaction products thereof), to produce a detectable electroactive reaction product. Typically, participation of the mediator in this reaction involves a change in its oxidation state (e.g., a reduction), upon interaction with any one of the analyte, the enzyme, or a cofactor, or a species that is a reaction product of one of these (e.g., a cofactor reacted to a different oxidation state).

A variety of mediators exhibit suitable electrochemical behavior. A mediator can be stable in its oxidized form or optionally may exhibit reversible redox electrochemistry. The mediator should exhibit good solubility in aqueous solutions and react rapidly to produce an electroactive reaction product. Examples of suitable mediators include, but are not limited to, benzoquinone, meldola blue, other transition metal complexes, potassium ferricyanide, and nitrosoanilines. See, e.g., U.S. Pat. No. 5,286,362.

In addition to the enzymes, mediators, and other detection reagent components, the test field may include carrier substances, auxiliary substances, pigments, fillers, buffer substances, etc., as are commonly known in the art. Hereinafter, no distinction is made between further substances that are likewise involved in the reaction for detecting the analyte, and the actual detection reagent.

It is to be appreciated that the chemistry of the reaction scheme of any chosen electrochemical detection method can be chosen in light of various chemical factors relating to the system, including the identity of the analyte and of the sample substance. Even then, for a given analyte or substance, various different reactive components may be useful in terms of a catalyst (often, a variety of enzymes will be useful), co-reactants (e.g., a variety of mediators may be useful), and cofactors (if needed, a variety may be useful). Many such reaction schemes and their reactive components and reaction products are known, and examples of a few different enzymes include those listed in Table 1.

TABLE 1

Exemplary Reaction Schemes for Test Elements.

| Analyte | Enzymes | Redox Mediator (Oxidized Form) | Additional Mediator |
|---|---|---|---|
| Glucose | glucose dehydrogenase and diaphorase | ferricyanide, osmium(III)-(bipyridyl)-2-imidazolyl-chloride, meldola blue, [Ru(NH$_3$)$_5$Melm]Cl$_3$[OS(III)(NH$_3$)5pyz]$_2$-(SO$_4$)$_3$, nitrosoaniline derivatives | N/A |
| Glucose | glucose oxidase | (see above) | N/A |
| Cholesterol | cholesterol esterase and cholesterol oxidase | (see glucose) | 2,6-dimethyl-1,4-benzoquinone, 2,5-dichloro-1,4-benzoquinone, or phenazine ethosulfate |
| HDL Cholesterol | cholesterol esterase and cholesterol oxidase | (see glucose) | (see above) |
| Triglycerides | lipoprotein lipase, glycerol kinase, glycerol-3-phosphate oxidase | (see glucose) | phenazine methosulfate, phenazine ethosulfate |

TABLE 1-continued

Exemplary Reaction Schemes for Test Elements.

| Analyte | Enzymes | Redox Mediator (Oxidized Form) | Additional Mediator |
|---|---|---|---|
| Triglycerides | Lipoprotein lipase, Glycerol kinase, Glycerol-3-phosphate dehydrogenase and Diaphorase | (see glucose) | (see above) |
| Lactate | lactate oxidase | (see glucose) | 2,5-dichloro-1,4-benzoquinone |
| Lactate | lactate dehydrogenase and diaphorase | (see glucose) | N/A |
| Lactate Dehydrogenase | diaphorase | (see glucose) | N/A |
| Pyruvate | pyruvate oxidase | (see glucose) | N/A |
| Alcohol | alcohol oxidase | (see glucose) | N/A |
| Alcohol | alcohol dehydrogenase and diaphorase | (see glucose) | N/A |
| Uric acid | uricase | (see glucose) | N/A |
| 3-Hydroxybutric acid (ketone bodies) | 3-hydroxybutyrate dehydrogenase and diaphorase | (see glucose) | N/A |

Another exemplary oxidation/reduction reaction scheme that is known to be useful for detecting glucose in a blood sample containing glucose uses an enzyme (e.g., glucose-dye-oxidoreductase (Gluc-Dor)) and optionally a cofactor (e.g., pyrrolo-quinoline-quinone (PQQ)) in the presence a redox mediator (e.g., benzoquinone, ferricyanide, or nitrosoaniline derivatives) to produce the oxidized form of the analyte, gluconolactone, and the reduced form of the redox mediator. See, e.g., U.S. Pat. No. 5,128,015.

Other examples of reaction schemes are known, and are typically used in methods designed to detect a specific analyte such as, for example, cholesterol, urea, etc.

Regardless of the dry-film reagent matrix used, a deliquescent material is added to the reagent matrix to protect components of the reagent from degradation by water. As noted above, deliquescent materials include sodium chloride, calcium chloride, magnesium chloride, magnesium sulfate, zinc chloride, potassium carbonate, potassium phosphate, carnallite, ferric ammonium citrate, potassium hydroxide and sodium hydroxide. As used herein, "deliquescence" means a phase transition from solid to solution that occurs when the vapor pressure of a saturated aqueous solution of a substance is less than the vapor pressure of water in ambient air. When water vapor is collected by the pure solid compound, a mixture of the solid and its saturated solution or an aqueous solution of the compound forms until the substance is dissolved and is in equilibrium with its environment. The relative humidity at which deliquescence occurs is a property of the specific substance. At this point the vapor pressure of water over the aqueous solution will equal the partial pressure of water in the atmosphere in contact with it. Accordingly, a salt particle will deliquesce in the atmosphere when the relative humidity surpasses the deliquescence point of the material. As used herein, "deliquescent material" thus generally means materials having deliquescent properties, and may refer to materials, such as salts, that have a strong affinity for moisture and that will absorb relatively large amounts of water from the atmosphere if exposed to it, thus protecting other materials from absorbing water.

As indicated above, the deliquescent material may be selected to be a material having a deliquescence point that protects the other reagent components when exposed to environmental humidity at a pre-determined level. Accordingly, in one aspect of the present disclosure, a user identifies a particular environmental stress to be avoided, such as the environmental stress of about 75% relative humidity, and includes in the reagent mixture a deliquescent material selected to have a deliquescence point at slightly below that level. For example, the deliquescence point of sodium chloride is near a relative humidity (RH) of about 75%, so the addition of sodium chloride is particularly effective for use with test elements that may be exposed to a relative humidity that may exceed about 75%. When the RH exceeds that point, the sodium chloride crystals absorb water faster than the other reagent materials, thus preempting absorption by the other components and protecting the other reagent materials from water degradation.

The amount of deliquescent material added to the reagent matrix will depend on the material being used, the other components in the reagent matrix, and the environmental conditions likely to be faced. In general, the deliquescent material will be provided in the reagent matrix in an amount effective to allow the deliquescent material to preemptively take on the water that would otherwise be taken on by other reagent components in the reagent matrix, and thus to prevent the other reagent components from deteriorating. In other words, the deliquescent material can be provided in an amount effective to absorb water from the atmosphere at a rate that is faster than the rate at which the other components of the reagent matrix absorb water from the atmosphere, thus preventing the other components from absorbing water and degrading.

In some instances, the deliquescent material may be a combination of two or more deliquescent materials. For example, a mixture of salts such as sodium chloride, magnesium sulfate and calcium chloride may be used.

Whether used individually or in combination, the deliquescent material(s) may be added to the reagent matrix in amounts effective to provide from about 1% to about 10% by weight percent deliquescent material in the dry film reagent, with amounts between about 2% and about 8% being desirable. In some instances, the deliquescent material is provided in the dry film reagent matrix in an amount between about 3% and about 7% by weight, with amounts between about 3% and about 6% being desirable. In other instances, the deliquescent material is included in the reagent material in an amount effective to provide at least about 2% deliquescent material in the dry film reagent matrix. In still other instances, the deliquescent material is included in the reagent material in an amount effective to provide at least about 3% deliquescent material in the dry film reagent matrix. Alternatively stated, the deliquescent material may be added to the reagent material in amounts effective to provide no more than about 10% deliquescent material in the dry film reagent matrix.

In an example below, the deliquescent material was provided in an amount effective to provide about 3.0% sodium chloride in the dry-film reagent matrix. In another example, the deliquescent material was provided in an amount effective to provide about 5.8% sodium chloride in the dry film reagent. In a third example, the deliquescent material was provided in an amount that provides about 6.5% magnesium sulfate in the dry-film reagent matrix.

As indicated above, the inventive concept described herein finds particular utility in stabilizing reagents used in a test element for detecting at least one analyte in a sample, such as detecting at least one metabolite in a body fluid, and particularly detecting glucose in a blood sample. Accordingly, certain aspects and principles of the inventive concept are illustrated herein by describing one particularly preferred embodiment, namely, an embodiment in which sodium chloride is used as a deliquescent material in a reagent mixture containing PVP or a PVP-containing material. By understanding the water sorption behavior of PVP and sodium chloride, the mechanism for improved mediator stability in films containing sodium chloride can be better understood. This understanding facilitates the design of reagent matrices when applied to the materials discussed above as well as new matrix components.

The methods can include the steps described herein, and these steps may be, but not necessarily, carried out in the sequence as described. Other sequences, however, also are conceivable. Furthermore, individual or multiple steps may be carried out either in parallel and/or overlapping in time and/or individually or in multiply repeated steps. Moreover, the methods may include additional, unspecified steps.

EXAMPLES

The inventive concept will be more fully understood upon consideration of the following non-limiting examples, which are offered for purposes of illustration, not limitation.

Example 1

Figure 2:
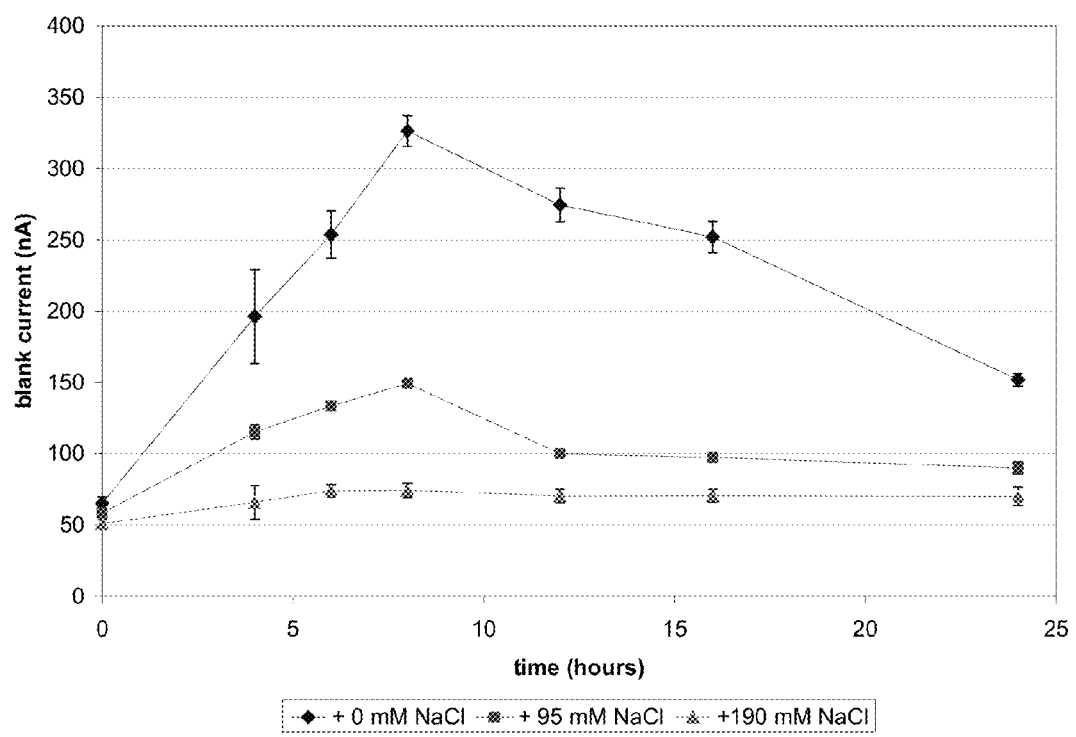
FIG. 2 shows a graph of the blank current (nA) over time for strips having varying amounts of sodium chloride added to the reagent mixture. The strips were dosed with unspiked blood and exposed to high heat and humidity conditions (30° C./80% RH).
Figure 3:
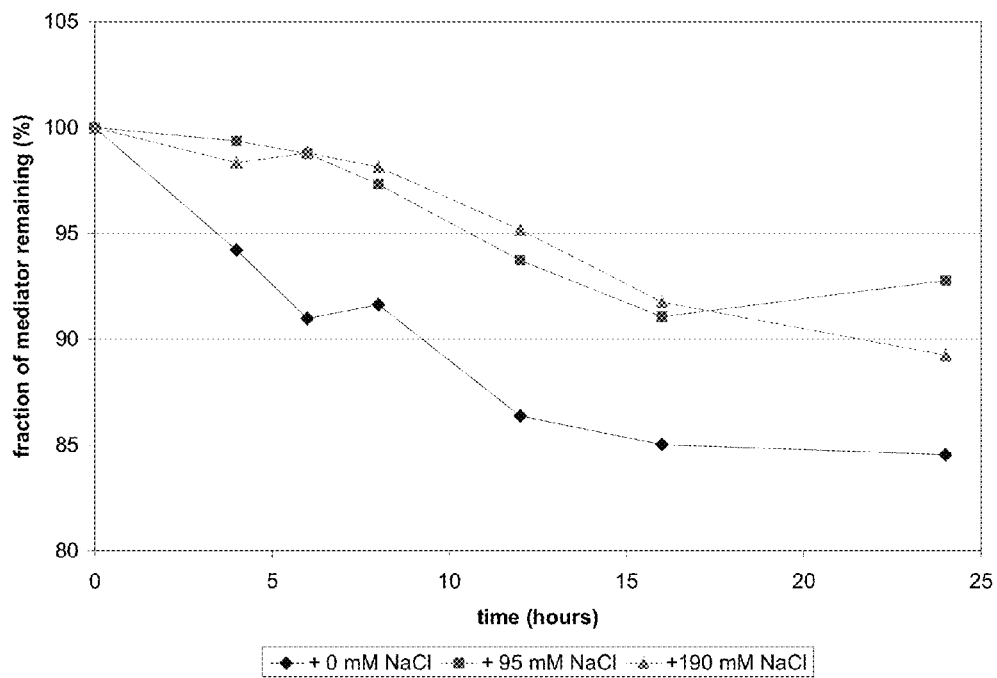
FIG. 3 shows a graph of the fraction of mediator remaining on the strip over time for strips having varying amounts of sodium chloride added to the reagent mixture. The strips were exposed to high heat and humidity conditions (30° C./80% RH).

Sodium chloride was added to the reagent to increase the ionic strength of the reagent. The blank current in both aqueous solution and in unspiked blood was significantly decreased in formulations that contained additional sodium chloride when compared to the formulation that did not contain additional sodium chloride (e.g., FIGS. 1 and 2). Mediator stability as measured independently by HPLC was better in strips with the additional sodium chloride, as shown in FIG. 3. The result is increased stability of the reagent matrix. As shown in FIG. 3, increasing the amount of a deliquescent material such as sodium chloride in a reagent matrix increases the fraction of mediator remaining on the strip after exposure to high humidity.

Example 2

Since exposure to high heat and humidity is known to cause mediator stability failure in glucose-specific test elements, the sorption behavior of PVP, sodium chloride, and mixtures of PVP and sodium chloride were studied. Such studies help characterize the sorption properties of the reagent matrix without studying the complete reagent matrix and are useful as a predictive tool for designing reagent matrix films with desirable water sorption characteristics.

The sorption isotherms of PVP and sodium chloride were measured and modeled, then compared with the measured sorption isotherms of mixtures of PVP and NaCl. Where appropriate, the measured data was modeled with the Flory-Huggins equation:

$$ln\, a_w = ln\, \phi_w + \phi_P + X_{wP} \cdot \phi_P^2,$$

where $a_w$ is the water activity in the gas phase (relative humidity), $\phi$ is the volume fraction of water (w) and polymer (P), and $X_{wP}$ is the interaction parameter between the water and polymer.

Figure 4:
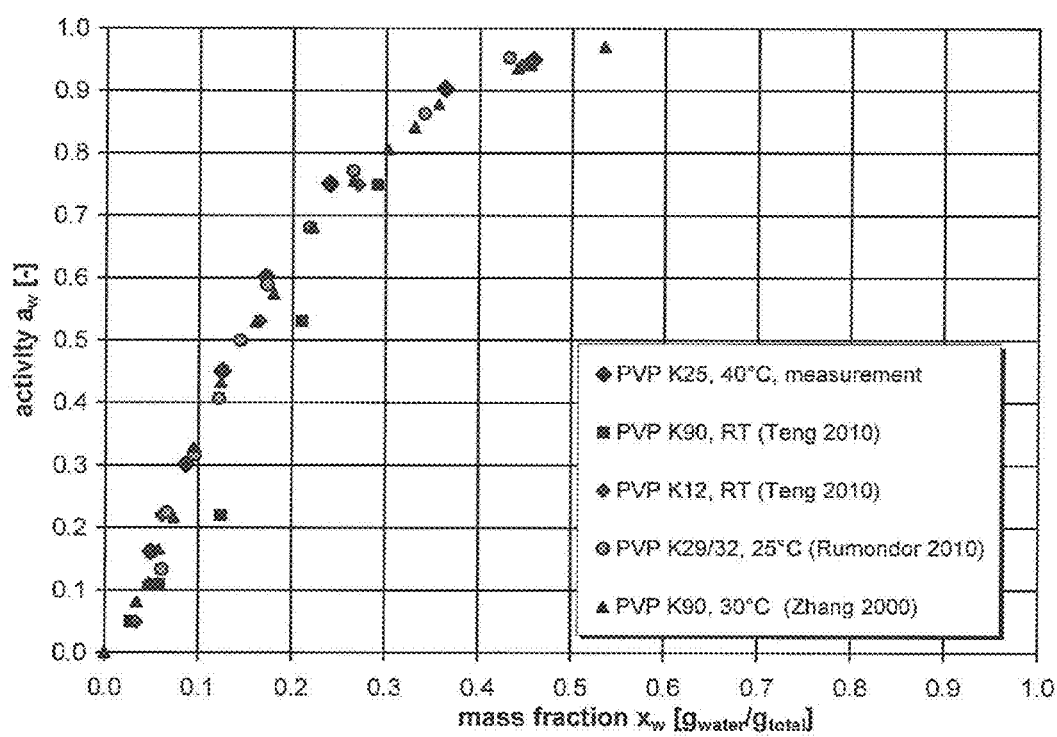
FIG. 4 is a graph of sorption data for PVP according to test measurements (diamonds) and reported literature values (other symbols).

The measured values and literature values corresponded well for PVP, as shown in FIG. 4, and the concentration dependence of the interaction parameter was found to fit the equation below. This equation was used to determine the amount of absorbed water by PVP in the mixtures.

$$X_{w,P} = 0.6954 - 0.1539 \cdot \phi_w - 0.0392 \cdot \phi_w^{-1}$$

Example 3

Sodium chloride does not adsorb appreciable amount of water below the deliquescence point. Accordingly, the amount of water adsorbed below the deliquescence point at relative humidity of 75% is, at most, a few molecular layers. Above the deliquescence point, the sodium chloride crystals dissolve and the concentration of the solution is a function of the water activity in the gas phase and is calculated as:

$$a_w = \gamma_w \cdot (1 - X_s),$$

where $X_s$ is the molar fraction of salt in the solution and $\gamma_w$ is the activity coefficient.

Figure 5:
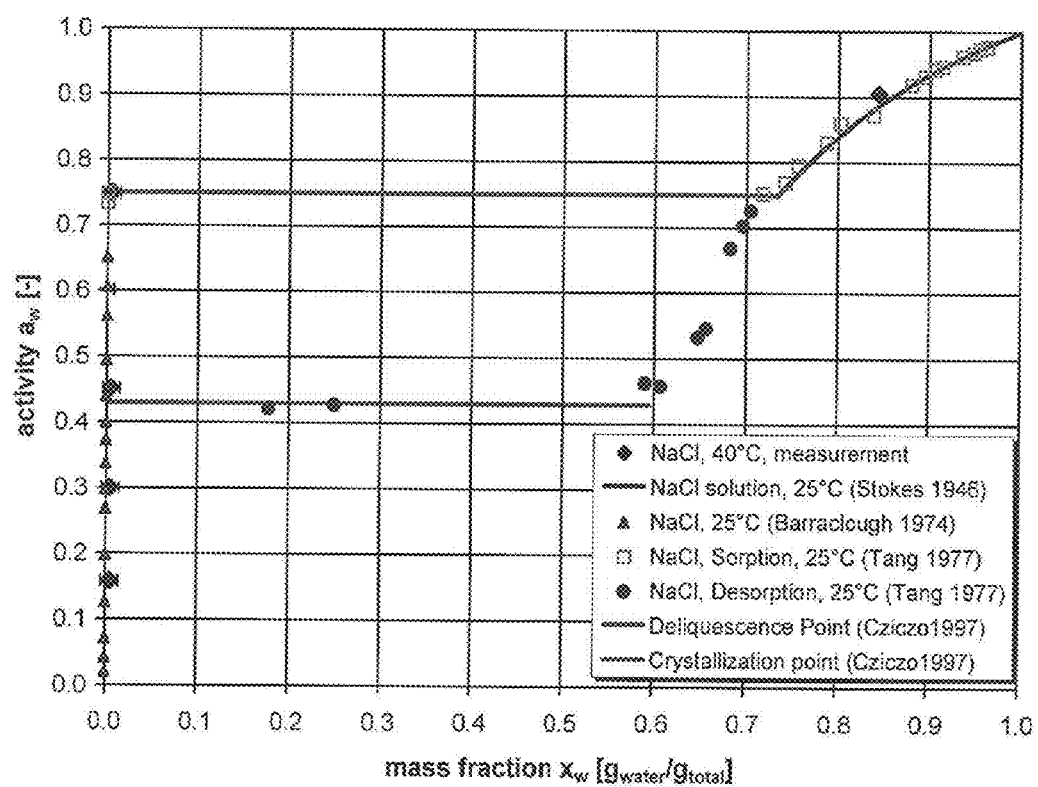
FIG. 5 is a graph of sorption data for sodium chloride according to test measurements (diamonds) and reported literature values (other symbols), as well as the deliquescence point and the crystallization point.

The activity coefficient was calculated from literature values and found to follow the following relationship to the water molar fraction (equation, FIG. 5):

$$\gamma w = -10.1757 x_w^2 + 20.9601 x_w + 9.7854.$$

Example 4

The sorption isotherms for PVP, sodium chloride, and mixtures of PVP and sodium chloride were compared. The results show that the mass of water adsorbed by the mixture is the weighted sums of the individual components. Below the deliquescence point of sodium chloride, the amount of water adsorbed by these mixtures decreases with the increasing amount of sodium chloride. However, the opposite is true at water activities above the deliquescence point of sodium chloride. Under these conditions, films with more sodium chloride have greater water sorption since sodium chloride adsorbs more water than PVP above the deliquescence point.

Figure 6:
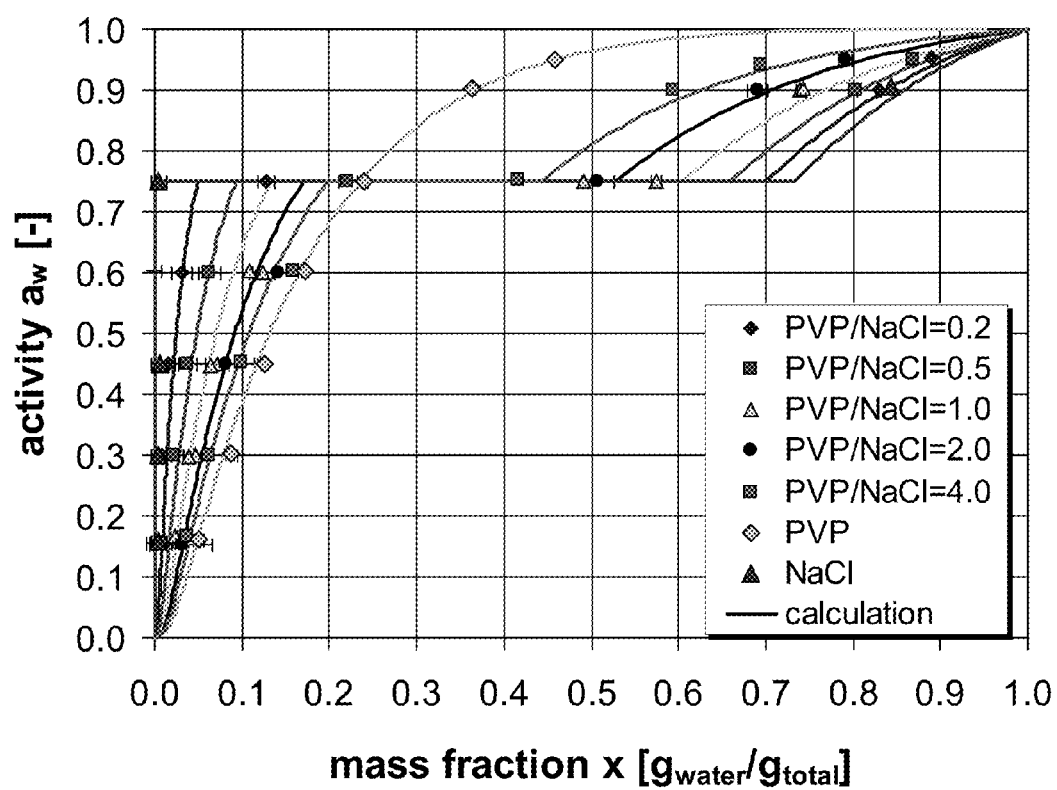
FIG. 6 is a graph of sorption isotherms for PVP, sodium chloride and mixtures of the two components.

The comparison of individual components and mixtures is shown in FIG. 6, where the PVP/sodium chloride ratio varied between 0.2 and 4.0. For the test elements described above, the PVP/sodium chloride ratio ranged from 1.7 to 3.4. As shown in FIG. 6, the addition of sodium chloride to PVP causes the resulting matrix to adsorb less water. This is shown by the fact that the curve for PVP (alone) is to the relative right in the figure, and increasing the sodium chloride ratio from 0.5:1, to 1:1, to 2:1, to 5:1 pushes the curve progressively to the left. Accordingly, it has been herein that the higher the concentration of salt in the matrix, the less water is adsorbed by the matrix.

Example 5

Deliquescent materials other than sodium chloride may also be used, as indicated above. For example, dry film reagents that are protected with a magnesium sulfate deliquescent material have been shown to be effective using the procedures described generally above. In particular, FIG. 7 shows that including magnesium sulfate in the dry film reagent matrix provides protection against water degradation in humid environments.

Figure 7:
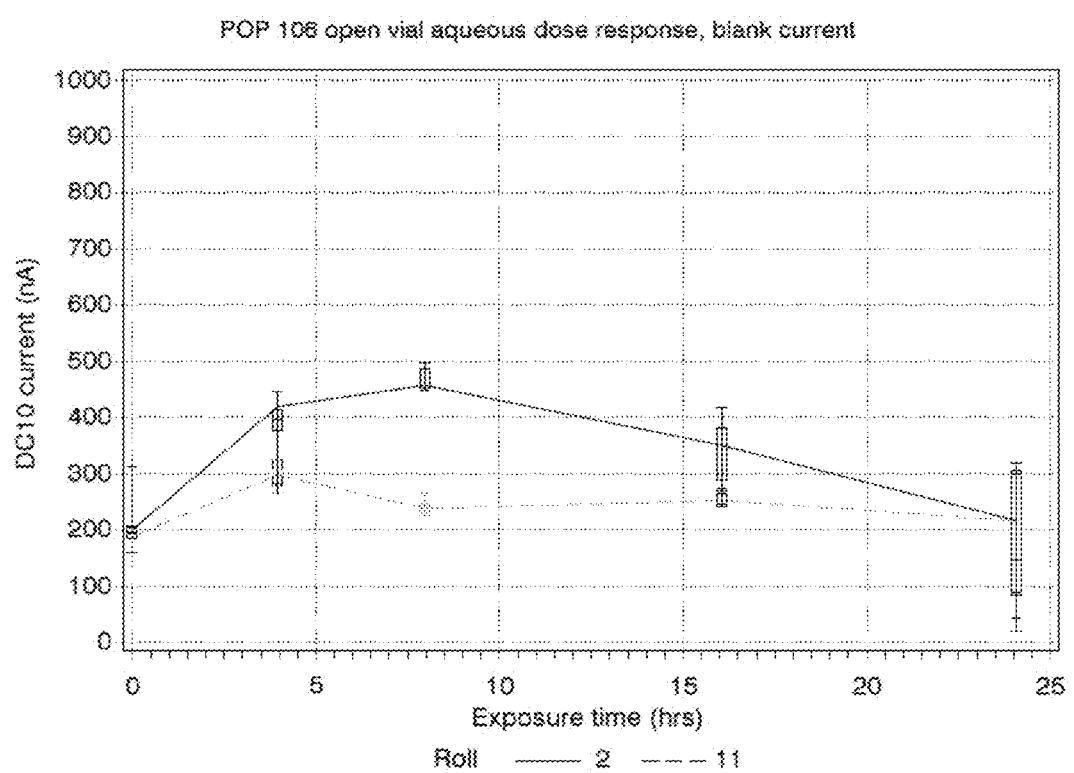
FIG. 7 is a graph of the blank currents observed when dry film reagent matrices having various additives are protected by deliquescent materials, as provided by certain aspects of the present disclosure.

In FIG. 7, roll 2 shows data from a test of a dry film reagent comprising a FAD-GDH enzyme/cofactor system, a nitrosoaline mediator, PVP, and no deliquescent material. In contrast, roll 11 shows data from a test of a dry film reagent having a reagent mixture that is comparable to the reagent mixture of roll 2, but with about 6% magnesium sulfate added as a deliquescent material. In these tests the temperature was about 30° C., and the RH was about 82%.

Inspection of the data provided in FIG. 7 shows a significantly higher blank current from roll 2, where the dry film reagent matrix does not include a deliquescent material, than for roll 11, where the dry film reagent matrix does include a magnesium sulfate deliquescent material. This indicates that including about 6% magnesium sulfate in the dry-film reagent mixture protects the reagent from degradation by water in the humid environment.

Additional work in the field of sorption isotherms is described in the following paper:
1. Kachel et al. (2013) *Chem. Eng. Process* 68:45-54.

Also, phase equilibrium data is reported in the following papers:
1. Cziczo et al. (1997) *J. Geophys. Res.* 102:18843-18850.
2. Barraclough & Hall (1974) *Surf. Sci.* 46:393-417.
3. Tang et al. (1977) *J. Aerosol Sci.* 8:149-159.
4. Stokes & Levien (1946) *J. Am. Chem. Soc.* 68:333-337.
5. Teng et al. (2010) *J. Pharm. Sci.* 99:3815-3825.
6. Zhang & Zografi (2000) *J. Pharm. Sci.* 89:1063-1072.
7. Rumondor et al. (2010) *J. Appl. Polym. Sci.* 117:1055-1063.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

The invention claimed is:

1. A test element for determining a presence or a concentration of an analyte in a sample fluid, comprising:
   at least one working electrode and at least one counter electrode disposed upon a substrate; and
   a dry-film reagent matrix extending between the at least one working electrode and the at least one counter electrode and configured for an electrode reaction, wherein the dry-film reagent matrix comprises a deliquescent material and one or more active ingredients effective for facilitating a desired electrochemical reaction, wherein the deliquescent material is sodium chloride, magnesium sulfate, or a combination thereof, wherein the deliquescent material is present in an amount effective to preemptively absorb water from the atmosphere when the relative humidity exceeds a predetermined level, and wherein the deliquescent material has a deliquescence point between about 50% relative humidity and about 80% relative humidity.

2. The test element of claim 1, wherein the deliquescent material has a deliquescence point at about 75% relative humidity.

3. The test element of claim 1, wherein the test element is a glucose-specific test strip, wherein the one or more active ingredients effective for facilitating the desired electrochemical reaction is a glucose reagent matrix comprising at least one enzyme system and at least one mediator.

4. The test element of claim 3, wherein the at least one enzyme system comprises a glucose dehydrogenase and a flavin adenine dinucleotide cofactor.

5. The test element of claim 3, wherein the at least one mediator comprises a nitrosoaniline.

6. The test element of claim 1, wherein the dry-film reagent matrix further comprises a film former comprising a polyvinylpyrrolidone (PVP) and/or a PVP-containing material.

7. The test element of claim 1, wherein the deliquescent material absorbs water from the atmosphere at a rate that is faster than a rate at which the other components of the reagent matrix absorb water from the atmosphere when the relative humidity in the atmosphere exceeds about 75%.

8. The test element of claim 1, wherein the deliquescent material absorbs water from the atmosphere at a rate that is faster than a rate at which the other components of the reagent matrix absorb water from the atmosphere when the relative humidity exceeds the deliquescence point of the deliquescent material.

9. The test element of claim 1, wherein the deliquescent material is in an amount from about 1% to about 10% by weight percent based on the total weight of the dry-film reagent matrix.

10. The test element of claim 1, wherein the deliquescent material is in an amount of at least about 2% by weight percent based on the total weight of the dry-film reagent matrix.

11. The test element of claim 1, wherein the deliquescent material is sodium chloride and is provided in an amount between about 3.0% by weight percent and about 6.0% by weight percent in the dry-film reagent matrix based on the total weight of the dry-film reagent matrix.

12. The test element of claim 1, wherein the deliquescent material is magnesium sulfate and is provided in an amount between about 3.0% by weight percent and about 7.0% by weight percent in the dry-film reagent matrix based on the total weight of the dry-film reagent matrix.

13. A method of improving stability of a test element with respect to degradation of reagent components by humidity in air, the method comprising the step of:

providing a test element comprising at least one working electrode and at least one counter electrode disposed on a substrate, and a dry-film reagent matrix extending between the at least one working electrode and the at least one counter electrode, wherein the dry-film reagent matrix comprises a deliquescent material in an amount effective to decrease the sorption of water from the air by other reagent components of the dry-film reagent matrix, and wherein the deliquescent material is sodium chloride, magnesium sulfate, or a combination thereof.

14. The method of claim 13, wherein the deliquescent material is sodium chloride and is provided in an amount between about 3.0% by weight percent and about 6.0% by weight percent in the dry-film reagent matrix based on the total weight of the dry-film reagent matrix.

15. The method of claim 13, wherein the deliquescent material is magnesium sulfate and is provided in an amount between about 3.0% by weight percent and about 7.0% by weight percent in the dry-film reagent matrix based on the total weight of the dry-film reagent matrix.

* * * * *